United States Patent [19]
Bishop et al.

[11] Patent Number: 5,486,166
[45] Date of Patent: Jan. 23, 1996

[54] FIBROUS NONWOVEN WEB SURGE LAYER FOR PERSONAL CARE ABSORBENT ARTICLES AND THE LIKE

[75] Inventors: David F. Bishop, Dunwoody; Clifford J. Ellis, Woodstock, both of Ga.

[73] Assignee: Kimberly-Clark Corporation, Neenah, Wis.

[21] Appl. No.: 386,244

[22] Filed: Feb. 9, 1995

Related U.S. Application Data

[63] Continuation of Ser. No. 206,986, Mar. 4, 1994, abandoned.

[51] Int. Cl.$^6$ .............................. A61F 13/15; A61F 13/20
[52] U.S. Cl. ........................ 604/366; 604/358; 604/365; 604/370; 604/378; 604/384; 604/367; 428/304.4; 428/311.1; 428/311.5; 428/311.7
[58] Field of Search ........................... 604/358, 365–367, 604/369–370, 374–375, 378, 384, 385.1; 428/304.4, 311.1, 311.5, 311.7, 314.8, 342

[56] References Cited

U.S. PATENT DOCUMENTS

| | | |
|---|---|---|
| 3,276,944 | 10/1966 | Levy . |
| 3,338,992 | 8/1967 | Kinney . |
| 3,341,394 | 9/1967 | Kinney . |
| 3,423,266 | 1/1969 | Davies et al. . |
| 3,502,538 | 3/1970 | Petersen . |
| 3,502,763 | 3/1970 | Hartmann . |
| 3,542,615 | 11/1970 | Dobo et al. . |
| 3,692,618 | 9/1972 | Dorschner et al. . |
| 3,802,817 | 4/1974 | Matsuki et al. . |
| 4,340,563 | 7/1982 | Appel et al. . |
| 4,488,928 | 12/1984 | Khan et al. . |
| 4,798,603 | 1/1989 | Meyer et al. ............................ 604/378 |
| 4,883,707 | 11/1989 | Newkirk .................................. 604/378 |
| 4,988,345 | 1/1991 | Reising . |
| 5,143,779 | 9/1992 | Newkirk et al. ....................... 604/378 |
| 5,188,624 | 2/1993 | Young, Sr. et al. ..................... 604/358 |
| 5,192,606 | 3/1993 | Proxmire et al. ....................... 604/378 |
| 5,198,057 | 3/1993 | Newkirk et al. ........................... 156/83 |

FOREIGN PATENT DOCUMENTS 803714  1/1969  Canada .

OTHER PUBLICATIONS

"Liquid Transport Through Fabrics; Wetting and Steady–State Flow Part I: A New Experimental Approach", Textile Research Journal, by Bernard Miller and David B. Clark, Mar. 1978, pp. 150–155.

"Adsorption of Gases in Multimolecular Layers", Journal of the American Chemical Society, Stephen Brunauer, P. H. Emmett and Edward Teller, Feb. 1938, vol. 60, pp. 309–319.

*Primary Examiner*—Randall L. Green
*Assistant Examiner*—P. Zuttarelli
*Attorney, Agent, or Firm*—Patrick C. Wilson

[57] ABSTRACT

Disclosed herein is a lofty fibrous nonwoven web which is particularly well-suited for use as a surge layer in personal care absorbent articles including, but not limited to, diapers, training pants, incontinence garments, sanitary napkins, bandages and the like. The fibrous nonwoven web is made from a plurality of fibers heat bonded to one another to form a lofty nonwoven web having a basis weight of at least 20 grams per square meter, a void volume of between about 80 and about 117 centimeters per gram of web while under a pressure of 689 dynes per square centimeter, a permeability of about 8,000 to about 15,000 darcy, a porosity of about 98.6 percent to about 99.4 percent and a surface area per void of about 10 to about 25 square centimeters per cubic centimeter. The fibrous nonwoven web will have a saturation capacity of between about 55 and about 80 grams of 0.9 percent saline solution per gram of web and a compression resilience in both the wet and dry state of at least about 60 percent.

16 Claims, 1 Drawing Sheet

5,486,166

FIBROUS NONWOVEN WEB SURGE LAYER FOR PERSONAL CARE ABSORBENT ARTICLES AND THE LIKE

This application is a continuation of application Ser. No. 08/206,986 entitled "Fibrous Nonwoven Web Surge Layer for Personal Care Absorbent Articles and the Like" and filed in the U.S. Patent and Trademark Office on Mar. 4, 1994, now abandoned.

FIELD OF THE INVENTION

The present invention is related to fibrous nonwoven webs which are useful in, among other things, personal care absorbent articles or products. More specifically, the present invention relates to a lofty fibrous nonwoven web which due to its unique design parameters is designed for rapid intake, retention and subsequent distribution of body exudates into the absorbent portion of the personal care article.

BACKGROUND OF THE INVENTION

Desired performance objectives for personal care absorbent products include low leakage from the product and a dry feel to the wearer. However, absorbent articles commonly fail before the total absorbent capacity of the product has been utilized. Absorbent garments, such as incontinence garments and disposable diapers, often leak at the legs and waist. The leakage can be due to a variety of shortcomings in the product, one being insufficient fluid uptake by the absorbent system, especially on the second or third liquid insults.

It had been found that urination can occur at rates as high as 15 to 20 milliliters per second and velocities as high as 280 centimeters per second. Conventional diaper absorbent structures, such as those comprising admixtures of absorbent gelling particles and cellulosic fluff pulp, may initially uptake fluids at rates of only 8 milliliters per second or less, based upon the web density and the concentration of the gelling particles. In addition, the initial uptake rates for conventional absorbent structures can deteriorate once they have already received liquid surges into their structures. The disparity between liquid delivery and uptake rates can result in excessive pooling on the surface of the fabric before the liquid is taken-up by the absorbent core. During this time, pooled liquid can leak from the leg openings of the diaper and soil the outer clothing and bedding of the wearer. Attempts to alleviate leakage have included providing physical barriers with such design features as elastic leg gathers and changing the amount and/or configuration of the absorbent material in the zone of the structure into which the liquid surges typically occur. Absorbent gelling particles have also been included to increase the liquid holding capacity in various regions of the absorbent structure, however, such absorbent gelling particles do not have the rapid uptake rates of conventional materials such as wood pulp and fluff which are also commonly used in absorbent cores. As a result, as the amount of absorbent gelling particles in the absorbent core structures are increased in modern day diapers, oftentimes the uptake rate will tend to decrease.

Nonwoven materials such as carded webs and spunbonded webs have been used as the body side liners in absorbent products. Specifically, very open, porous liner structures have been employed to allow liquid to rapidly pass through them and to help keep the body skin separated from the wetted absorbent pad underneath the liner. In addition, other layers of material, such as those constructed with thick, lofty fabric structures, have been interposed between the liner and absorbent pad for the purpose of reducing wet back.

With conventional fluff-based absorbent structures, the cellulosic fibers when wetted can lose resiliency and therefore collapse. As a result, the liquid uptake rate of the wetted structures may become too low to adequately accommodate subsequent liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake liquid.

The addition of more absorbent materials, such as secondary fluff pledgets, or absorbent gelling particles, have been employed to increase holding capacity. The desired rate of liquid intake within such arrangements, however, may not be sufficiently sustained during successive liquid surges.

Despite the development of absorbent structures of the types surveyed above, there remains a need for improved absorbent structures which can adequately reduce the incidents of leakage from absorbent products such as disposable diapers. There is therefore a need for a material and resultant product which can provide effective handling of liquid surges and which can more effectively uptake and retain repeated loadings of liquid during use.

SUMMARY OF THE INVENTION

Personal care absorbent articles such as diapers, training pants, incontinence garments and sanitary napkins are often required to accept quick, large insults of body exudates which are beyond the short term absorptive capacity of the product. As a result, it has been found advantageous to use surge layers within such personal care absorbent articles.

Personal care absorbent articles generally have a fluid permeable body side liner and a liquid impermeable backing layer with an absorbent core disposed therebetween. The material of the present invention is used as a surge layer disposed between the body side liner and the absorbent core. In addition, it is helpful if the surge layer of the present invention is attached to the liner and the absorbent core to promote liquid transfer.

To perform in the desired manner, the fibrous nonwoven web should be made from or include a plurality of thermoplastic fibers heat bonded to one another to form a lofty nonwoven web having a basis weight of at least 20 grams per square meter. In more refined embodiments the basis weight will range from about 40 to about 68 grams per square meter. The web can be made entirely from bicomponent fibers which are typically crimped and which will generally have a fiber denier equal to or greater than 2. Alternatively, the web can be made from a combination of fibers such as bicomponent fibers and polyester fibers. In such embodiments, the web will usually include at least 50 percent by weight bicomponent fibers. The resultant web will have a void volume of between about 80 and about 117 cubic centimeters per gram of web at 689 dynes per square centimeter pressure, a permeability of about 8,000 to about 15,000 darcy, a porosity of about 98.6 to about 99.4 percent, a surface area per void volume of about 10 to about 25 square centimeters per cubic centimeter, a saturation capacity between about 55 and about 80 grams of 0.9 percent saline solution per gram of web and a compression resilience in both the wet and dry state of at least about 60 percent.

DETAILED DESCRIPTION OF THE INVENTION

Figure 1:
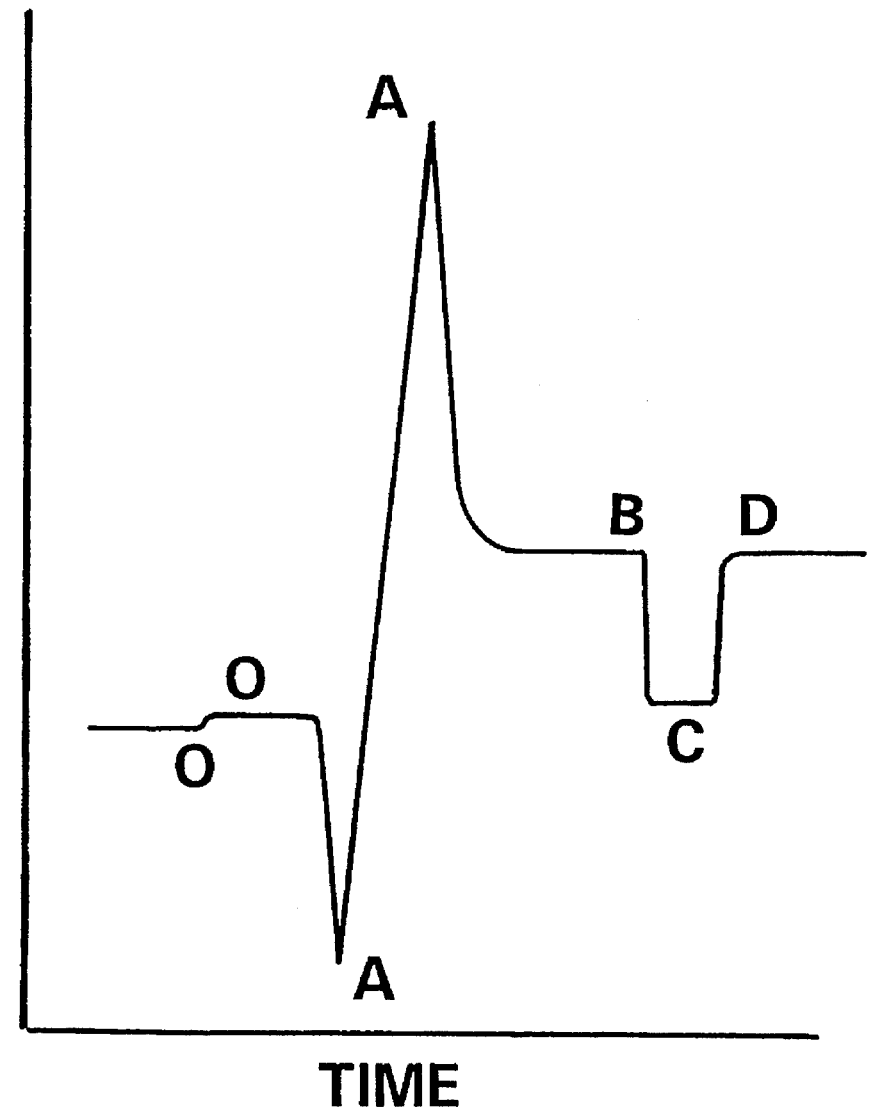
FIG. 1 is a graph depicting fluid pressure versus time. The graph is used in conjunction with the calculation of perme-

The present invention is directed to a lofty fibrous nonwoven web which is particularly well-suited for use as a surge layer in personal care absorbent articles including, but not limited to, diapers, training pants, incontinence garments, sanitary napkins, bandages and the like.

Personal care absorbent articles typically include a liquid permeable body side liner and a liquid impermeable backing layer or baffle with an absorbent core disposed therebetween. As discussed in the background, a common problem with many of these products and their designs is the fact that they will not accept rapid and/or multiple insults of body fluids or exudates such as menses and urine in a sufficiently short period of time without leaking. In an attempt to overcome this problem, many product designs have included some sort of additional layer between the body side liner and the absorbent core to act as a dash pot of sorts to temporarily absorb, hold and then discharge the particular body exudate taken in from the liner. The present invention relates to a lofty fibrous nonwoven web which has been specifically designed and, which when incorporated into a personal care absorbent article or product, provides an effective means for temporarily storing and then distributing body exudates. This material is referred to as a surge layer.

The fibrous nonwoven web of the present invention is used as a surge layer disposed between the body side liner and the absorbent core. The surge layer is most typically placed between and in contact with the body side liner and the absorbent core though other additional layers may be incorporated into the overall product design if so desired. To further enhance fluid transfer, it is desirable that the fibrous nonwoven web surge layer be attached to the layers directly above and below its exterior surfaces. To this end, suitable attachment means include, but are not limited to, adhesives (water-based, solvent-based and thermally activated adhesives), thermo bonding, ultrasonic bonding, needling and pin aperturing as well as combinations of the foregoing or other appropriate attachment means.

The processes used to form the fibrous nonwoven web include those which will result in a material which, as further described below, is very lofty and open in nature. Suitable processes include, but are not limited to, airlaying, spunbonding and bonded carded web formation processes. Spunbond nonwoven webs are made from fibers which are formed by extruding a molten thermoplastic material as filaments from a plurality of fine capillaries in a spinneret with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563, Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent Number 803,714 which are all incorporated herein by reference in their entirety.

The spunbond process also can be used to form bicomponent spunbond nonwoven webs as, for example, from side-by-side polyethylene/polypropylene spunbond bicomponent fibers. The process for forming such fibers and resultant webs includes using a pair of extruders for separately supplying both the polyethylene and the polypropylene to a bicomponent spinneret. Spinnerets for producing bicomponent fibers are well known in the art and thus are not described herein in detail. In general, the spinneret includes a housing containing a spin pack which includes a plurality of plates having a pattern of openings arranged to create flow paths for directing the high melting temperature and low melting temperature polymers to each fiber-forming opening in the spinneret. The spinneret has openings arranged in one or more rows and the openings form a downwardly extending curtain of fibers when the polymers are extruded through the spinneret. As the curtain of fibers exit the spinneret, they are contacted by a quenching gas which at least partially quenches the fibers and develops a latent helical crimp in the extending fibers. Oftentimes the quenching air will be directed substantially perpendicularly to the length of the fibers at a velocity of from about 100 to about 400 feet per minute at a temperature between about 45° and about 90° F.

A fiber draw unit or aspirator is positioned below the quenching gas to receive the quenched fibers. Fiber draw units or aspirators for use in meltspinning polymers are well known in the art. Exemplary fiber draw units suitable for use in the process include linear fiber aspirators of the type shown in U.S. Pat. No. 3,802,817 to Matsuki et al. and eductive guns of the type shown in the U.S. Pat. Nos 3,692,618 to Dorshner et al. and 3,423,266 to Davies et al. all of which are incorporated herein by reference in their entirety. The fiber draw unit in general has an elongated passage through which the fibers are drawn by aspirating gas. The aspirating gas may be any gas, such as air that does not adversely interact with the polymers of the fibers. The aspirating gas can be heated as the aspirating gas draws the quenched fibers and heats the fibers to a temperature that is required to activate the latent crimps therein. The temperature required to activate the latent crimping within the fibers will range from about 110° F. to a maximum of less than the melting point of the low melting component polymer which, in this case, is the polyethylene. Generally, a higher air temperature produces a higher number of crimps per unit length of the fiber.

The drawn and crimped fibers are deposited onto a continuous forming surface in a random manner, generally assisted by a vacuum device placed underneath the forming surface. The purpose of the vacuum is to eliminate the undesirable scattering of the fibers and to guide the fibers onto the forming surface to form a uniform unbonded web of bicomponent fibers. If desired, the resultant web can be lightly compressed by a compression roller before the web is subjected to a bonding process.

To bond the bicomponent spunbonded web a through-air bonder is used. Such through-air bonders are well known in the art and therefore need not be described herein in detail. In the through-air bonder, a flow of heated air is applied through the web to heat the web to a temperature above the melting point of the lower melting point component of the bicomponent fibers but below the melting point of the higher melting point component. Upon heating, the lower melting polymer portion of the web fibers are melted and the melted portions of the fibers adhere to adjacent fibers at the crossover points while the high melting polymer portions of the fibers tend to maintain the physical and dimensional integrity of the web.

Bonded carded webs are made from staple fibers which are usually purchased in bales. The bales are placed in a picker which separates the fibers. Next, the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed through the web and then activated, usually by heating the web and adhesive with hot air. Another bonding method is pattern bonding wherein heated calendar rolls or ultrasonic bonding equipment are used to bond the fibers together, usually in a localized bond pattern though the web can be bonded across its entire surface if so desired. The best method though, when using bicomponent staple fibers is to use a through-air bonder such as is described above with respect to the bicomponent spunbond web formation process.

In order to maintain the lofty and open nature of the resultant fibrous nonwoven web according to the present invention, the bonding process used to bond the fibers of the fibrous nonwoven web together should be a process such as through-air bonding which does not unduly compress or collapse the structure during the formation process. In through-air bonding, heated air is forced through the web to melt and bond together the fibers at their crossover points. Typically the unbonded web is supported on a forming wire or drum. In addition a vacuum may be pulled through the web if so desired to further contain the fibrous web during the bonding process.

Bonding processes such as point bonding and pattern bonding using smooth and/or pattern bonding rolls should generally be avoided if such processes will create a resultant fibrous nonwoven web which is too dense and does not have the degree of voids necessary for the present invention. Whatever process is chosen, the degree of bonding will be dependent upon the fibers/polymers chosen but, in any event, it is desirable that there be as little compression as possible during the heating stage.

Airlaying is another well known process by which fibrous nonwoven webs according to the present invention can be made. In the airlaying process, bundles of small fibers usually having lengths ranging between about 6 and about 19 millimeters are separated and entrained in an air supply and then deposited onto a forming screen, oftentimes with the assistance of a vacuum supply. The randomly deposited fibers are then bonded to one another using, for example, hot air or a spray adhesive.

In order to form a fibrous nonwoven web with the parameters outlined below, at least a portion of the fibers forming the web must be made from polymers which are heat bondable. By heat bondable it is meant that the randomly deposited fibers forming the nonwoven web can be subjected to heat or ultrasonic energy of a sufficient degree that the fibers will adhere to one another at the fiber cross over points due to the melting or partial softening of the polymer forming the heat bondable fibers. Suitable polymers for forming such heat bondable fibers are permanently fusible and are typically referred to as being thermoplastic. Examples of suitable thermoplastic polymers include, but are not limited to, polyolefins, polyesters, polyamides, orlon, acetates and polyvinyl alcohol as well as homopolymers, copolymers and blends. In addition, wetting agents/surfactants may be added either internally, such as with siloxane during the fiber formation process, or externally as a post treatment either to the fibers and/or the resultant web as with anionic or nonionic surfactants including fluorocarbons. Such wetting agents/surfactants as well as their use are well known and need not be described herein in detail.

The fibers formed from the aforementioned polymers may be short staple length fibers such as are used in the airlaying and the bonding and carding processes or longer more continuous fibers as are formed in, for example, the spunbond process. Typical staple fiber lengths will range between about 38 and about 51 millimeters, though lengths outside this range also may be used. For example, airlaying typically involves using fibers with lengths in the range of about 6 to about 19 millimeters. Fiber diameters will be governed by the surface area to void volume parameters set forth below. Typically the fiber diameters will range between about 1.5 and about 16 denier with the target range being between about 3 and about 6 denier.

In order to achieve the lofty open structure of the material of the present invention, it is desirable that the fibers be crimped. Crimping can be imparted both mechanically and chemically thereby forming both zig zag or saw tooth and helically or spirally crimped fibers. Fiber cross-sections may be either circular or noncircular including, for example bilobal, trilobal, and X-shaped cross-sections. The fibers may be solid or hollow. In addition they may be made from a single fiber polymer or from multiple polymers such as are commonly found in biconstitutent and bi- or multicomponent fibers. When using bicomponent fibers, fiber cross-sections may include, for example, sheath/core, side-by-side and islands-in-the-sea cross-sections.

The resultant fibrous nonwoven web will generally be a homogenous single layer blend of whatever type fiber or fibers are chosen. It is also possible, however, to form multilayer structures provided they meet the parameters set forth with respect to the present invention.

To facilitate the through-air bonding process, it has been found advantageous to use bicomponent fibers which have both a higher melting point and lower melting point component such as in a side-by-side, sheath/core or islands-in-the-sea configurations. The lower melting point component or polymer of the bicomponent fibers provides an efficient means for bonding the fibers together while the higher melting point component aids in maintaining the structural rigidity and the openness of the material both in the dry and wet states. Suitable bicomponent fibers include, for example, whether in staple fiber or more continuous spunbond form, polyethylene/polypropylene and polyethylene/polyester fibers. The fibrous nonwoven web according to the present invention may be made entirely from bicomponent fibers or it may be made from a blend of bicomponent fibers and other fibers such as single component fibers including polyesters, nylons, rayons and polyolefins such as polypropylene. It also may be made exclusively from single component fibers. Generally, the fibrous nonwoven web according to the present invention will include at least 50% by weight bicomponent fibers, based upon the total weight of the web. Such bicomponent fibers will typically have an average denier equal to or greater than 2.

The material of the present invention has been designed based upon a specific set of parameters. These parameters include basis weight, void volume, permeability, porosity, surface area per void volume, hydrophilicity, compression resiliency and saturation capacity. The basis weight of the fibrous nonwoven web according to the present invention will be at least 20 grams per square meter with no real upper limit and with the target range being from about 40 to about 68 grams per square meter. The void volume of the fibrous nonwoven web is a measure of how much air space there is in the structure. The void volume as explained in the test procedures below is measured at 689 dynes per square centimeter (0.01 pounds per square inch) and will range from about 80 to about 117 cubic centimeters per gram of web with the target range being from about 80 to about 100 cubic centimeters per gram of web. The permeability indicates the ability of the structure to conduct fluid through it. When a fluid initially enters a surge structure, fluid movement is dominated by forced flow from the momentum of the fluid. Capillarity may not be significant in this flow regime as it may not have enough time to control the fluid path, thus, fluid flow through the structure will be controlled by the permeability of the structure on the initial insult. A high permeability value indicates that it is relatively easy for a fluid to flow through the structure. Permeability for the materials according to the present invention will range between about $7.8 \times 10^{-5}$ to about $1.5 \times 10^{-4}$ square centimeters (8,000 to 15,000 darcy). Outside this range other materials have been found not to work as well.

The porosity of the nonwoven web is the ratio of the amount of void space in a web to the total volume of the web. The porosity of the materials according to the present invention, as measured at a pressure of 689 dynes per square centimeter (0.01 pounds per square inch), will range from about 98.6% to about 99.4%.

The surface area per void volume with the void volume being measured at 689 dynes per square meter (0.01 pounds per square inch) pressure will range from about 10 to about 25 square centimeters per cubic centimeter. Permeability is the result of fluid having to travel over and around fiber surfaces when under forced flow in order to occupy the void spaces within the web. Surface area per void volume (SA/VV) indicates how closely together those fiber surfaces are located to each other. Thus, SA/VV can control the amount of permeability for a structure. A high SA/VV value indicates there is a large amount of surface area which is placed closely together. Increases in SA/VV can be achieved by using smaller fibers which increases the surface area per unit weight or by making the structure more dense which decreases the void volume per unit weight. When SA/VV is increased, permeability decreases since fluid is forced to travel over and around more surfaces to get through the structure. If the SA/VV becomes too high, then the permeability will be too low to allow easy fluid entry into and flow through the surge structure. Thus, SA/VV must stay below 25 cm²/cc in order for the permeability to be above about 8,000 darcy.

To ensure rapid intake of liquid, the overall structure must have hydrophilic tendencies. At least a portion of the fibers must have a contact angle less than 90 degrees. As a result, a fibrous nonwoven web according to the present invention will have sufficient hydrophilic tendencies when the web has a saturation capacity greater than 55 grams of 0.9% saline solution per gram of web. Another important feature of the material of the present invention is its resiliency in both the wet and dry states. A unique feature of the present invention is the amount of liquid which the material is able to absorb upon rapid insult. In addition, once the liquid has been absorbed, the material of the present invention does not readily collapse which would be detrimental to the overall performance of the material in that the collapsing of the material would result in a reduced capacity for retaining liquid. Materials according to the present invention should have compression resilience values in both the wet and dry states of at least about 60%.

In order to demonstrate the properties of the present invention, a series of materials were formed and then tested relative to whether they met the parameters outlined above. In addition, samples of these materials were then placed within diaper constructions and tested for leakage properties. The test procedures, materials and test results are set forth below.

VOID VOLUME AND COMPRESSION RECOVERY/RESILIENCY TEST

Void volume and compression recovery were measured using an INSTRON or SINTECH tensile tester to measures the resisting force as a material is compressed between a movable platen and a fixed base at a constant rate using a certain amount of force and subsequently releasing the force at the same rate. Preferably pressure, or force, and platen position are recorded. If only force is recorded, pressure is calculated using:

$$P = \frac{F}{A_p \cdot 10,000 \text{ cm}^2/\text{m}^2}$$

where:
P=pressure in Pascals
F=force pushing back on the platen in Newtons
$A_p$=area of the platen in square centimeters (18.9 cm²)

Void volume for a given platen position is calculated using the equation:

$$VV = \frac{(x_o - x) \cdot A_m \cdot 0.1 \text{ cm/mm}}{M} - \frac{1}{\rho_{fiber}}$$

where:
VV=void volume of material in cubic centimeters per gram
$x_o$=initial platen position from the base in millimeters
x=platen position from initial position in millimeters
$A_m$=area of material in square centimeters
M=mass of material in grams
$\rho_{fiber}$=fiber density in grams per cubic centimeter For webs made with multiple fiber types, the web fiber density is the weight average of each individual fiber density:

$$\rho_{fiber,Total} = \text{wt }\%_{fiber\ 1} \cdot \rho_{fiber\ 1} + \text{wt }\%_{fiber\ 2} \cdot \rho_{fiber\ 2} + \cdots$$

where:
wt %=weight percent of the fiber type in the web or:

$$\text{wt \%} = \frac{\text{fiber weight in composition}}{\text{total composition weight}} \times 100\%$$

The base must be larger in size than the platen. Zero height between platen and base distance was set by bringing the platen down until it barely touches the base. The platen was then raised to the desired initial height from the zero distance. The initial platen position must be greater than the initial thickness of the material so that the test starts out at zero pressure on the sample. The material can be the same size as the platen or larger.

Suitable equipment for this test could include:
Compression tester:
  INSTRON model 6021 with compression test software and 1 kN load cell made by Instron of Bucks, England.
Balance:
  Mettler of Highstown, N.J., model PM4600

For the purpose of measuring void volume for the present specification, a 4.9 cm diameter circular platen was used to compress materials against the base at a rate of 5.08 mm/min up to 909 gm load (4,690 Pascal or 0.68 pounds per square inch pressure). The platen was then returned at the same rate to the initial starting position. The initial starting position for the platen was 12.7 mm from the base. Material samples were cut to 10.2 cm×10.2 cm and tested in the center. Force and position data were recorded every 0.03 minutes or every 0.15 mm. Five repeats were performed on separate material pieces.

Wet void volume was measured similarly to the dry void volume except the sample was completely immersed in 0.9% saline throughout the test. A flat bottomed container such as a hexagonal polystyrene weighing dish catalog #02-202D from Fischer Scientific of Pittsburgh, Pa. was placed on the base and the platen was zeroed and set to the initial position as described in the dry void volume method. 0.9% saline was added to the container to fill it to a level just to the bottom of the platen at its initial position. At this point in the procedure the load cell was tared. An appropriate saline, could be S/P certified blood bank saline made by Stephens Scientific of Riverdale, N.J. and distributed by Baxter Healthcare of McGraw Park, Ill. under catalog #B3158-1. The load cell was tared with this level of fluid in the container. The sample was placed in the fluid, under the platen and the test was then performed as described above for the dry void volume. Buoyant force was found to have a negligible affect on pressure but if so desired it can be subtracted from the pressure readings at each platen position using the following equation:

$$P_B = \rho_{saline} \cdot g \cdot (x_o - x) \cdot \left| \frac{A_p}{A_d - A_p} + 1 \right| \cdot 0.01$$

where:

$P_B$=Pressure from buoyant force in Pascals
$\rho_{saline}$=saline (fluid) density in grams per cubic centimeter
$A_p$=area of the platen in square centimeters (18.9 cm$^2$)
$A_d$=area of the dish in square centimeters
$x_o$=initial platen position from the base in millimeters
x=platen position in millimeters
g=standard acceleration of gravity which is 981 centimeters per seconds squared
0.01=conversion factor=0.1 cm/mm·0.001 kg/gm·100 cm/m The overall pressure on the sample becomes:

$$P_{sample} = P_{reading} - P_B$$

where:

$P_{sample}$=pressure on the sample from the platen in Pascal
$P_{reading}$=pressure reading from the SINTECH or INSTRON in Pascal
$P_B$=buoyancy pressure from the 0.9% saline in Pascal For the purpose of measuring void volume for the present specifications, 120 ml of saline was placed in the container and the platen was initially set 12.7 mm from the base.

Percent recovery at 68.9 Pascal (0.01 psi) was calculated using the platen positions on compression and recovery when the pressure was 68.9 Pascal:

$$\% \text{ Recovery} = \frac{VV_{recovery\ 68.9\ Pa}}{VV_{compress\ 68.9\ Pa}}$$

where:

$VV_{recovery\ 68.9\ Pa}$=void volume upon recovery at 68.9 Pascal pressure
$VV_{compress\ 68.9\ Pa}$=void volume upon compression at 68.9 Pascal pressure

POROSITY CALCULATION

Porosity is the ratio of the amount of void space in a web to the total volume of that web, or:

$$\phi = (1 - \rho_{web}/\rho_{fiber}) \cdot 100\%$$

where:

$\phi$=porosity of the web and is dimensionless
$\rho_{web}$=web density in grams per cubic centimeter
$\rho_{fiber}$=fiber density in grams per cubic centimeter If a web is made of multiple fiber types with different densities, then the total fiber density is the weight average of the individual fiber densities:

$$\rho_{fiber,\ Total} = wt\ \%_{fiber\ 1} \cdot \rho_{fiber\ 1} + wt\ \%_{fiber\ 2} \cdot \rho_{fiber\ 2} + \cdots$$

where:

wt %=weight percent of the fiber type in the web

The void volume of the web can be used to calculate porosity instead of the web density:

$$\phi = 1 - \frac{1}{\rho_{fiber} \cdot (VV - 1/\rho_{fiber})} \cdot 100\%$$

where:

VV=void volume of the web in cubic centimeters per gram of web. Void volume is calculated in accordance with the procedures set forth under the "Void Volume and Compression Recovery/Resiliency Test" above.

As a material becomes more open in structure, the porosity will approach the asymptote one, indicating empty space.

PERMEABILITY TEST

Permeability indicates the ease or difficulty with which a fluid flows through a structure when a pressure gradient is applied to a fluid. The resulting fluid velocity through the structure is controlled by the permeability of the structure. The permeability of these samples in the Z-direction, which is through the thickness of the material, was measured by a forced flow test which is described in detail in an article by Bernard Miller and David B Clark entitled, "Liquid Transport Through Fabrics; Wetting and Steady-State Flow" published in *Textile Research Journal*, pages 150 through 155, (March 1978). The foregoing article is incorporated herein by reference in its entirety.

To perform the test, a forced flow resistance monitor was built in accordance with the instructions in the foregoing article. In the forced flow test, the sample was held in a cylinder and fluid was pushed through the material at a constant velocity by a piston and the back pressure against the piston was recorded. The permeability was calculated using Darcy's Law which describes fluid flow through a porous medium according to the following equation:

$$v = \frac{Q}{A} = -\frac{k_z}{\mu} \cdot \frac{dp}{dz}$$

where:

v=superficial flow velocity or piston velocity in centimeters per minute
Q=volume flow rate in cubic centimeters per second
A=cross sectional area of the inner diameter of the tube (31.7 square centimeters)
$k_z$=material permeability constant
dp=pressure drop minus the average wall resistance pressure, both in Pascals
z=thickness in centimeters of the material. Sum of all layers.
dp/dz=pressure gradient across the material in Pascals per centimeter μ=fluid viscosity (cp) which is about 6 cp for Penetek oil This equation can in turn be solved for permeability in the Z-direction ($k_z$) in the units of darcy as follows:

$$k_z = \frac{v \cdot \mu}{\frac{dp}{dz}} \cdot \frac{0.001 \text{ Pa} \cdot \text{sec/cp}}{60 \text{ sec/min}} \cdot 1.032 \times 10^8 \text{ darcy/cm}^2$$

The pressure drop for the test was obtained using a plot of the pressure vs. time. The pressure drop is equal to the change in pressure between the pause point C in FIG. 1 of the drawings and when the piston starts up again at point D in FIG. 1. The wall resistance which was subtracted from the pressure drop was measured by running the test without a sample in the cylinder and measuring the same pressure drop. The measurement of the wall resistance was done five times and then averaged.

The thickness of the material can be obtained either by performing the compression resiliency test described above at a maximum pressure of 689 dynes per square centimeter (0.01 pounds per square inch) on each sample, or measuring the sample's basis weight and using the average specific volume (inverse density) from the compression resiliency test. The thickness calculation for the latter method is:

$$z = \frac{M}{A_{sample}} \cdot \overline{V}_{sp, 68.9 \, Pa}$$

where:

M=mass of material in grams $A_{sample}$=area of sample which was 45.6 square centimeters $\overline{V}_{sp, 68.9 \, Pa}$=average specific volume for the material from the compression resiliency test at 68.9 Pascals (0.01 pounds per square inch) in cubic centimeters per gram of web Since the standard deviation of the specific volume at 68.9 Pascal was less than ten percent of the average, the assumption of constant specific volume was considered to be valid. If the specific volume standard deviation is above ten percent, then it must be measured directly using the compression resiliency test described above. When two or more samples were layered, the samples were oriented with their machine directions from formation in the same direction and stacked on top of each other top-to-bottom (i.e. the air side from formation to the wire side from formation).

The equipment used in conjunction with the test apparatus included a pressure transducer Model #P3061-50WD from Lucas-Schaevitz Company of Pennsauken, N.J. This pressure transducer was capable of measuring up to 50 inches of water (12,440 Pa) pressure. The additional equipment used included a chart recorder Model SE 120, 881221100 from BBC Goerz Metrawatt of Austria; a slide and motor positioner model #B4036W1J from Velmex, Inc. of Holcomb, N.Y.; a stepper motor controller model #14V 8K BASIC from Centroid Corporation of State College, Pa.; and, a COMPAQ® personal computer with a serial port.

Calibration of the pressure measurements was accomplished by adding a known weight or volume of fluid to the cylinder and comparing the pressure transducer response to the theoretical pressure increase using the formula:

$$\Delta P_{theory} = \rho \cdot g \cdot h = g \cdot M/A \cdot 100 \text{ cm/m} \cdot 0.001 \text{ kg/gm}$$

where:

$\Delta P_{theory}$=theoretical pressure change in Pascals

ρ=fluid density in grams per cubic centimeter g=standard acceleration of gravity which is 981 centimeters per square second h=height of fluid added to cylinder in centimeters A=inner area of cylinder in square centimeters which was 31.7 square centimeters M=fluid mass in grams The Pressure change from the transducer and strip chart recorder was calculated using the equation:

$$\Delta P_{trans} = \frac{\text{Chart}_{read}}{FS_{chart}} \cdot \frac{\text{Chart}_{volt}}{PT_{volt}} \cdot PT_{pres} \cdot 248.8 \text{ Pa/in H}_2\text{O}$$

where:

$\Delta P_{trans}$=pressure transducer reading in Pascals $\text{Chart}_{read}$=chart reading on x-y plotter in number of gradations $FS_{chart}$=full scale (total gradations) on x-y plotter in number of gradations $\text{Chart}_{volt}$=chart recorder full scale voltage setting in millivolts $PT_{volt}$=pressure transducer full scale voltage range in millivolts $PT_{pres}$=pressure transducer full scale pressure range in inches of water In deriving the permeability data, no screens were used to hold the samples in place. Instead, two halves of a 6.35 cm inner diameter cylinder which screwed together with a 7.62 cm diameter sample positioned between the two cylinder pieces. Mineral oil was used as the fluid. Specifically, the mineral oil was Penetek technical grade mineral oil from Penreco of Los Angeles, Calif. The mineral oil had a viscosity of approximately 6 centipoise. The piston velocity was 20 cm/min. The results given in the data section were the average of the results of five separate tests on five separate samples of material and were reported in darcy.

SURFACE AREA PER VOID VOLUME CALCULATION (SA/VV)

Surface areas of fabrics composed of round cross-section staple fibers can be calculated directly. The surface area is calculated from fiber denier using the relationship:

$$SA = \left| \frac{\text{Denier}}{\rho_{fiber} \text{ g/cc}} \right|^{1/2} \cdot (1/\text{Denier}) \cdot 3363$$

where:

SA=surface area in square centimeters per gram of web or fabric

Denier=fiber size in denier which is the weight in grams of a single fiber 9000 meters in length $\rho_{fiber}$=fiber density in grams per cubic centimeter 3363=conversion factor from square root Denier divided by Denier to square root of diameter (in centimeters) divided by length (in centimeters)

If the surge material is made of a blend of fibers, then the total surface area per unit weight for the material is the weight average:

$$SA_{total} = wt \, \%_{fiber \, 1} \cdot SA_{fiber \, 1} + wt \, \%_{fiber \, 2} \cdot SA_{fiber \, 2} + \ldots$$

where:

$SA_{total}$=total surface area in the web in cm²/g wt $\%_{fiber \, 1}$=weight percent of the fiber in the web $SA_{fiber \, 1}$=surface area of the fiber in cm²/g The fiber-surface-areas within webs composed of modified cross-section fibers, such as modified cross-section staple fibers, modified cross-section melt extruded fibers can be measured by the BET method of Brunauer, Emmett and Teller, *Journal of the American Chemical Society*, 60, 309 (1938) which is incorporated herein by reference in its entirety.

The BET technique involves the absorption of a monomolecular layer of gas molecules on to the surface of the fibers. Calculations regarding the amount of gas present on the fibers yields a quantification of the fiber surface area values. This method has been used fairly routinely in the paper industry for fibrous webs, such as papers, fillers and filter materials.

SA/VV then is the calculated ratio of the fiber surface area per unit weight (square centimeter per gram) to the web's void volume per unit weight (cubic centimeters per gram). SA/VV thus has the units of square centimeters per cubic centimeters.

SATURATION CAPACITY TEST

The saturation capacity test measures the saturation capacity of the material while in the horizontal plane and under a no load condition. The no load horizontal saturation capacity test takes a small sample of material, places it in a liquid environment and measures the maximum amount of liquid the material will hold. The value obtained is a result of the interaction between the void volume, pore size distribution and wettability of the material.

The equipment and materials include a pan measuring at least 15 cm wide×20 cm long×5 cm deep. The pan should not be greater than 10 cm deep. A second pan measuring at least 12 cm wide×12 cm long×1.3 cm with a maximum depth not exceeding 10 cm. It is best if this pan is made from a lightweight material as it will be involved in the weighing process. Also needed is a balance readable to 0.01 grams and the balance should be covered so that the air currents do not affect the readings. Lastly, a saline solution is needed such as 0.9 per cent S/P Certified Blood Bank Saline Solution Catallog B3158-1 from Baxter Healthcare Corporation.

Sample preparations involved cutting samples of the materials to be tested. The dimensions of the samples should be 10 cm×10 cm square. The first pan measuring 15×20 cm×5 cm should be filled with the above identified saline solution to within 1.3 cm from the top of the pan.

Each sample should be individually weighed on the balance and the weight recorded as the dry weight. Next, the tare weight of the dry 12 cm×12 cm×1.3 cm pan should be measured and recorded. The tare 12 cm×12 cm×1.3 cm pan is placed next to the 15 cm×20 cm×5 cm pan. Care should be taken to wipe up any spilled liquid on the surface upon which the tared pan is placed as this will affect the tare weight.

A sample is placed into the pan containing the saline solution and is allowed to remain in the solution undisturbed until it becomes submerged or for a maximum of 15 seconds, whichever occurs first. If the sample floats on top of the solution it should not be forced down into the solution as a floating sample is an indication of an insufficiently hydrophilic material. Once the sample has completely submerged or the 15 second period has elapsed, the sample should be withdrawn from the saline solution by using both hands and grabbing the sample at all four corners using the middle and index finger to grab one corner of one side and the thumb and ring finger for grabbing the other corner on the same side. The sample should be lifted from the solution and placed in the tared pan as quickly as possible. Next, the wet sample should be weighed, the tare weight subtracted and the wet weight recorded. The above procedure is repeated until all samples are tested. As a special note, most of the samples being tested will contain a surfactant which will wash out into the saline solution. As a result, the solution should be changed after approximately 40 samples have been wetted or when the level in the pan drops to about 2.5 cm.

To calculate the saturation capacity, the wet weight for each sample is divided by the dry weight and the number one is then subtracted from the result to eliminate the contribution of the dry weight in the numerator. The resultant number is the saturation capacity of the material which is recorded as grams of liquid per grams of sample.

EXAMPLES

Having described the test procedures for evaluating the parameters of the materials according to the present invention, a series of sample materials were prepared and tested for their properties. A summary of these materials and their properties is set forth below. Six sample materials were prepared including both single-layer and two-layer fibrous nonwoven webs. The target basis weight for Examples 1 and 3 through 6 was approximately 50 grams per square meter. The actual basis weights are given in Table 1. The target basis weight for Example 2 was 80 grams per square meter with the actual value being 83.4 grams per square meter (gsm). In examples 3 and 4, a two-layer structure was created with the first layer being approximately 13 grams per square meter and the second layer being approximately 37 grams per square meter. All samples were prepared using conventional carding equipment and were subsequently through-air bonded at temperatures and times sufficient to cause the lower melting point component of the bicomponent fibers to at least partially melt and bond to one another at their crossover points.

In Example 1, a 50.5 gsm fibrous nonwoven web was created using a homogeneous blend of 60 percent by weight 4.4 denier by 38 mm millimeter soft 71 polypropylene fibers from Danaklon a/s of Denmark and 40 weight percent 3.0 denier by 38 millimeter polyethylene sheath/polyester core bicomponent fibers from BASF Corporation Fibers Division of Enka, N.C. Both these fibers, as with all fibers contained within the examples, contained a manufacturer's finish which made the fibers hydrophilic. All fibers were targeted by the manufacturer to have contact angles less than 90°. The two fibers were uniformly mixed together, carded and then bonded using hot air at a temperature of approximately 143° C. for 4 seconds to bond the overall structure. The void volume, surface area per void volume, porosity, permeability and saturation capacity values for this material are set forth in Table 1.

In Example 2, an 83.4 gsm single-layer fibrous nonwoven web was made using 20 percent by weight 6.0 denier by 51 millimeter Hoechst Celanese type 293 polyester staple fibers from Hoechst Celanese Textile Fibers Group of Charlotte, N.C.; 60 percent by weight of the previously-described 3.0 denier BASF bicomponent fibers and 20 percent by weight 1.5 denier by 38 millimeter Hoechst Celanese type 183 polyester staple fibers from Hoechst Celanese Textile Fibers Group of Charlotte N.C. As with Example 1, these fibers were uniformly mixed together, carded and then bonded using hot air at a temperature of approximately 135° C. for approximately 4 seconds. The properties of this material are set forth in Table 1.

In Example 3, a two-layer structure was created including a first layer of the previously described three-denier BASF polyethylene sheath/polyester core bicomponent fibers having a basis weight of approximately 13 gsm. Next, a second layer was formed on top of the first layer and the two layers were then bonded together using hot air at approximately 129° C. for approximately 4 seconds. The second layer contained a uniform mixture of 20 percent by weight of the previously-described Hoechst Celanese type 293 six-denier polyester fibers; 35 percent by weight of the BASF three-denier polyethylene sheath/polyester core bicomponent fibers; 40 percent by weight of the Hoechst Celanese type 183 1.5-denier polyester fibers and 5 percent by weight of 2.0 denier by 38 millimeter polyethylene sheath/polypropylene core ES-HB bicomponent fibers from Chisso Corporation of Osaka, Japan. The combined layers had a basis weight of 46.1 grams per square meter and the parameters for this material are set forth in Table 1.

In Example 4, a second two-layer structure was created. This two-layer structure most closely resembles the current material being used in the commercially-available diapers of the assignee of record. The top layer was approximately 17 grams per square meter and contained the three-denier BASF polyethylene sheath/polyester core bicomponent fibers. The second or bottom layer contained a homogeneous mix of 60 percent by weight of the Hoechst Celanese 6.0 denier type 295 polyester fibers; 35 percent by weight of a 1.7 denier by 38 millimeter polyethylene sheath/polypropylene core type ES bicomponent fiber from Chisso Corporation of Osaka, Japan and 5 percent by weight of the 2.0 denier Chisso-type ES-HB polyethylene sheath/polypropylene core bicomponent fibers. The two layers were bonded together in the same manner and using the same conditions as the material described in Example 3, and the resultant material had a basis weight of 46.1 grams per square meter. The test results are set forth in Table 1.

In Example 5, a single layer fibrous nonwoven web having a basis weight of 49.8 gsm was created using a uniform mixture of 40 percent by weight Hoechst Celanese type 224 6.0-denier polyester staple fibers and 60 percent by weight of a Chisso-type ES P 3.0-denier by 38 millimeter polypropylene sheath/polypropylene core bicomponent fiber. The web was bonded using hot air at a temperature of 135° C. for approximately 4 seconds. The test results for this material are set forth in Table 1.

In Example 6, a homogeneous single-layer fibrous nonwoven web having a basis weight of 51.9 gsm was created using 20 percent by weight of the Hoechst Celanese type 295 6.0-denier polyester fibers; 20 percent by weight of the Hoechst Celanese type 183 1.5 denier polyester fibers and 60 percent by weight of the BASF 3.0-denier polyethylene sheath/polyester core bicomponent fibers. The homogeneous blend of fibers was bonded together using hot air at a temperature of 135° C. for approximately 4 seconds. The test results for this material are set forth in Table 1.

TABLE 1

| EXAMPLE | BASIS WT. gsm | VOID VOL. cc/g | SA/VV cm²/cc | POROSITY % | PERMEABILI DARCY | SAT CAP g/g | COMP RES % dry | COMP RES % wet |
|---|---|---|---|---|---|---|---|---|
| 1 | 50.5 | 32 | 54.2 | 97.0 | 2569 | 21 | 93 | 89 |
| 2 | 83.4 | 60 | 29.6 | 98.7 | 5528 | 44 | 75 | 76 |
| 3 | 46.1 | 68 | 29.7 | 98.9 | 5565 | 46 | 71 | 75 |
| 4 | 46.1 | 60 | 19.4 | 98.6 | 6647 | 49 | 73 | 78 |
| 5 | 49.8 | 84 | 20.0 | 98.9 | 9256 | 59 | 76 | 76 |
| 6 | 51.9 | 110 | 16.2 | 99.3 | 13,189 | 79 | 70 | 73 |

The fibrous nonwoven webs according to the present invention must have a basis weight of at least 20 grams per square meter, a void volume between about 80 and about 117 cubic centimeters per gram of web at a pressure of 689 dynes per square meter (0.01 lbs. psi), a permeability of about 8,000 to about 15,000 darcy, a porosity of about 98.6% to about 99.4% and a surface area per void volume of about 10 to about 25 square centimeter per cubic centimeters. Referring to Table 1, it can been seen that the material defined in Example 1 had surface area per void volume, porosity and permeability values which were all outside this range. With respect to Example 2, it can be seen that only the conditions for porosity were met. For Example 3, the same was also true. Sample 4 came closer to meeting the parameters of the present invention but still failed to meet the void volume and saturation capacity and permeability parameters with respect to the present invention.

Example 5 demonstrates all the properties of the present invention. The same was true with respect to Example 6. In addition, the materials of Examples 5 and 6 both had sufficient degrees of both wet and dry compression resiliency. The wet and dry resiliency values for Example 5 were respectively 76% and 76% while the wet and dry compression resiliency values for Example 6 were 73% and 70%. Both of these materials therefore met the requirement that the compression resilience in either the wet or dry state be at least 60%.

Example 5 was put into HUGGIES® Ultratrim Step 4 diapers as a surge material between the body side liner and the absorbent core. The surge material was lightly glued to both the liner and absorbent core using National Starch 34-5563 spray from the National Starch Company of Bridewater, N.J. The add-on level for the adhesive between the liner and the surge material according to the present invention was approximately 0.01 to 0.04 grams per diaper while the add-on level between the surge layer and the tissue-wrapped absorbent core was approximately 0.03 to 0.05 grams per diaper. These diapers were use tested and were found to have a 6.4% overall leakage occurrence for males and a 3.7% overall leakage occurrence for females. These overall leakage numbers are considered excellent given the current state of the art in disposable diaper leakage protection.

Having thus described the invention in detail, it should be apparent that various other modifications and changes can be made in the present invention without departing from the spirit and scope of the following claims.

We claim:

1. A fibrous nonwoven web comprising:

a plurality of thermoplastic fibers heat bonded to one another to form a lofty nonwoven web having a basis weight of at least 20 grams per square meter, a void volume of between about 80 and about 117 cubic centimeters per gram of web at 689 dynes per square centimeter pressure, a permeability of about 8,000 to about 15,000 darcy, a porosity of about 98.6% to about 99.4% and a surface area per void volume of about 10 to about 25 square centimeters per cubic centimeter.

2. The fibrous nonwoven web of claim 1 wherein said basis weight ranges from about 40 to about 68 grams per square meter.

3. The fibrous nonwoven web of claim 1 wherein said web has a saturation capacity between about 55 and about 80 grams of 0.9 percent saline solution per gram of web.

4. The fibrous nonwoven web of claim 3 wherein said web has a compression resilience of at least about 60 percent.

5. The fibrous nonwoven web of claim 1 wherein said web includes at least 50% by weight bicomponent fibers, based upon the total weight of said web.

6. The fibrous nonwoven web of claim 5 wherein at least a portion of said bicomponent fibers have a denier equal to or greater than 2.

7. The fibrous nonwoven web of claim 5 wherein said web further includes polyester fibers.

8. The fibrous nonwoven web of claim 5 wherein said bicomponent fibers are crimped.

9. A personal care absorbent article comprising:
a body side liner and a backing layer with an absorbent core disposed therebetween, said article further including a surge layer disposed between said body side liner and said absorbent core, said surge layer comprising a plurality of thermoplastic fibers heat bonded to one another to form a lofty nonwoven web having a basis weight of at least 20 grams per square meter, a void volume of between about 80 and about 117 cubic centimeters per gram of web at 689 dynes per square centimeter pressure, a permeability of about 8,000 to about 15,000 darcy, a porosity of about 98.6% to about 99.4% and a surface area per void volume of about 10 to about 25 square centimeters per cubic centimeter.

10. The personal care absorbent article of claim 9 wherein said basis weight ranges from about 40 to about 68 grams per square meter.

11. The personal care absorbent article of claim 9 wherein said web has a saturation capacity between about 55 and about 80 grams of 0.9 percent saline solution per gram of web.

12. The personal care absorbent article of claim 11 wherein said web has a compression resilience of at least about 60 percent.

13. The personal care absorbent article of claim 9 wherein said web includes at least a 50% by weight bicomponent fibers, based upon the total weight of said web.

14. The personal care absorbent article of claim 13 wherein at least a portion of said bicomponent fibers have a denier equal to or greater than 2.

15. The personal care absorbent article of claim 13 wherein said web further includes polyester fibers.

16. The personal care absorbent article of claim 13 wherein said bicomponent fibers are crimped.

* * * * *